US008319198B2

(12) United States Patent
Bert et al.

(10) Patent No.: US 8,319,198 B2
(45) Date of Patent: Nov. 27, 2012

(54) DEVICE AND METHOD FOR DETERMINING CONTROL PARAMETERS FOR AN IRRADIATION UNIT, IRRADIATION UNIT AND IRRADIATION METHOD

(75) Inventors: Christoph Bert, Aschaffenburg (DE); Elke Rietzel, Weiterstadt (DE); Alexander Gemmel, Erlangen (DE); Nami Saito, Darmstadt (DE)

(73) Assignees: GSI Helmholtzzentrum fur Schwerionenforschung GmbH (DE); Siemens, AG (DE)

( * ) Notice: Subject to any disclaimer, the term of this patent is extended or adjusted under 35 U.S.C. 154(b) by 0 days.

(21) Appl. No.: 13/123,632

(22) PCT Filed: Oct. 8, 2009

(86) PCT No.: PCT/EP2009/007244
§ 371 (c)(1), (2), (4) Date: Aug. 30, 2011

(87) PCT Pub. No.: WO2010/043340
PCT Pub. Date: Apr. 22, 2010

(65) Prior Publication Data
US 2011/0303858 A1    Dec. 15, 2011

(30) Foreign Application Priority Data

Oct. 13, 2008 (DE) .......................... 10 2008 051 476

(51) Int. Cl.
*G21G 5/00* (2006.01)
*A61N 5/00* (2006.01)
*A61N 5/10* (2006.01)
(52) U.S. Cl. .................................. 250/492.3; 250/505.1
(58) Field of Classification Search ............... 250/492.1, 250/492.2, 492.3, 505.1
See application file for complete search history.

(56) References Cited

U.S. PATENT DOCUMENTS
6,509,573 B1 *  1/2003  Badura et al. .............. 250/492.3
(Continued)

FOREIGN PATENT DOCUMENTS
DE        10031074 A1    1/2002
(Continued)

OTHER PUBLICATIONS

Keall, PJ, etal. "Motion Adaptive X-ray Therapy: a Feasibility Study" In: Phys.Med.Biol.46(2001)1-10 Inst.ofPhysicsPublishing PII:S0031-9155(01)16478-X.

(Continued)

*Primary Examiner* — Bernard E Souw
(74) *Attorney, Agent, or Firm* — Reising Ethington PC

(57) ABSTRACT

The invention concerns a device for determining control parameters for an irradiation system by means of which a number of irradiation doses are successively deposited at different target points in a target volume. The device comprises an input device which is designed for detecting a target region and for detecting a movement of the target region, an evaluation device for detecting control parameters for controlling a beam in such a way that with the help of the control parameters a beam is able to follow the movement of the target region and to deposit a defined dose distribution in the target region, wherein the evaluation device is designed in such a way that when detecting the control parameters at least a first selectable control parameter is detected so that the beam is able to follow the movement of the target region merely orthogonally to beam direction, or when detecting the control parameters, at least a first selectable control parameter and a further control parameter representing energy modulation are detected, wherein the determination of the at least first control parameter and the further control parameter is performed by considering motion tracking in beam direction.

13 Claims, 4 Drawing Sheets

U.S. PATENT DOCUMENTS

Figure 1:
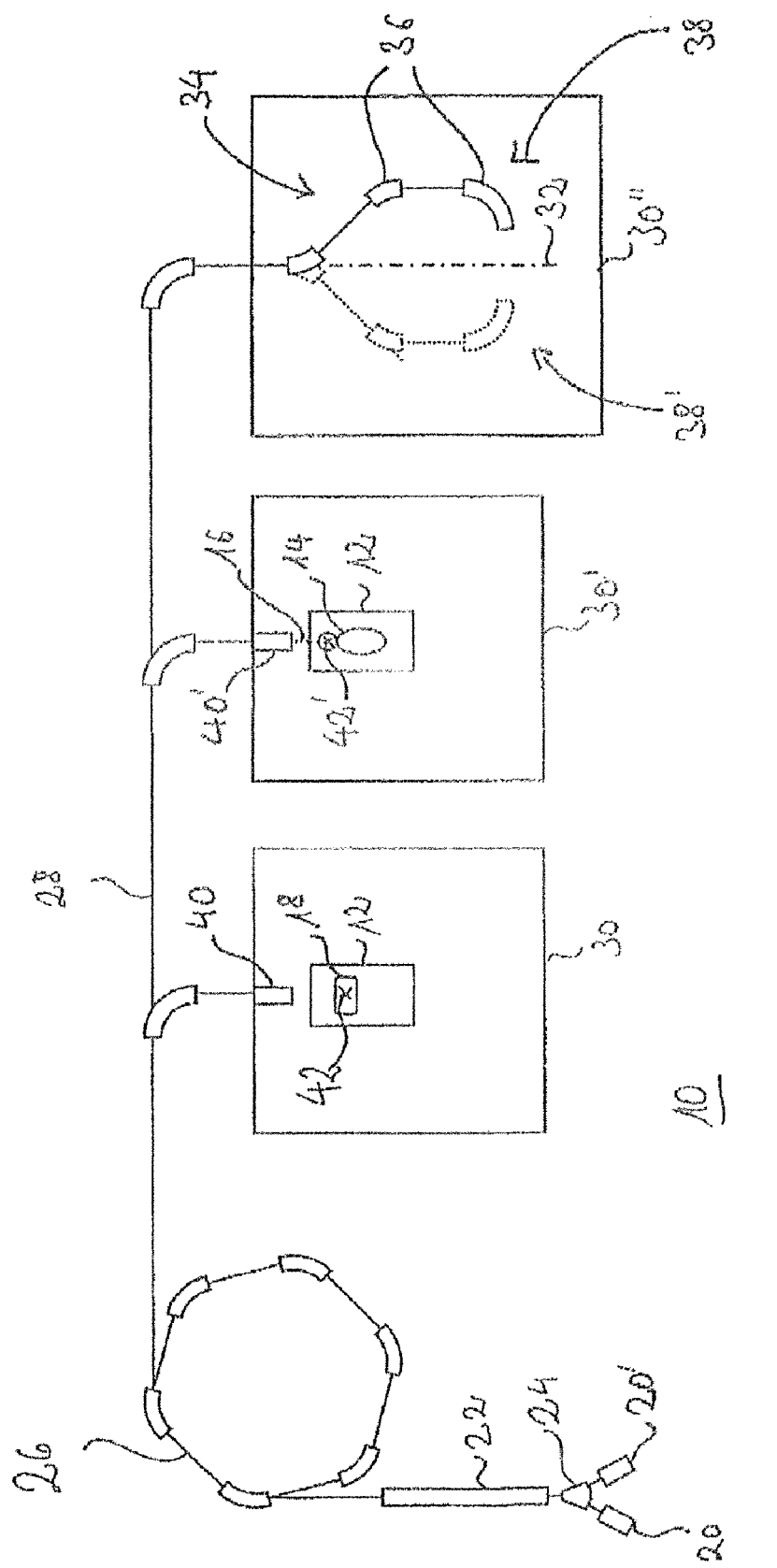

| | | | |
|---|---|---|---|
| 6,710,362 B2 * | 3/2004 | Kraft et al. | 250/492.3 |
| 6,891,177 B1 * | 5/2005 | Kraft et al. | 250/505.1 |
| 7,257,191 B2 * | 8/2007 | Sommer | 378/65 |
| 7,482,606 B2 * | 1/2009 | Groezinger et al. | 250/492.3 |
| 2006/0033042 A1 | 2/2006 | Groezinger et al. | |
| 2010/0108903 A1 * | 5/2010 | Bert et al. | 250/396 R |
| 2010/0301235 A1 * | 12/2010 | Bert et al. | 250/492.3 |
| 2011/0272600 A1 * | 11/2011 | Bert et al. | 250/492.1 |
| 2012/0029862 A1 * | 2/2012 | Scholz et al. | 702/127 |
| 2012/0187314 A1 * | 7/2012 | Bert et al. | 250/492.3 |

FOREIGN PATENT DOCUMENTS

| | | |
|---|---|---|
| DE | 102004028035 A1 | 12/2005 |
| DE | 102005063220 A1 | 6/2007 |
| WO | WO 0207817 A2 | 1/2002 |
| WO | WO 2007079854 A2 | 7/2007 |

OTHER PUBLICATIONS

McQuaid, D and Webb,S "IMRT Delivery to a Moving Targert by Dynamic MLC Tracking . . . " In:Phys.Med.Biol.51(2006)4819-4839 Inst.ofPhys.Pub.

Bert, Christoph, etal "Target MotionTracking with a Scanned Particle Beam" Medical Physics Ltr In: 4768-4771 Med.Phys.34(12), Dec. 2007.

Grozinger, S, et al. "3D Online Compensation of Target Motion with Scanned Particle Beam" In:Radiother Oncol.73,2004, S. S77-S79.

* cited by examiner

- Beam inbound direction
- Number of areas
- Overlap of individual rasterpoints
- Rescanning
- Adjustment of scan path
- Combination of Gating and Tracking
- Combination of merely orthogonal tracking and a tracking in beam direction
- Adjustment of scan speed

Fig. 4

DEVICE AND METHOD FOR DETERMINING CONTROL PARAMETERS FOR AN IRRADIATION UNIT, IRRADIATION UNIT AND IRRADIATION METHOD

The invention concerns a device and a method for determining control parameters for an irradiation system. Such a device or such a method is especially used in the context of particle therapy, for example, in the context of therapy planning in which control parameters are determined in the preparation process of irradiation. These control parameters make it possible that subsequently, during the irradiation process, a specific object can be irradiated according to specific presets. Furthermore, the invention concerns an irradiation system and an irradiation method.

The particle therapy is an established method for treating tissue, especially tumor diseases. However, the irradiation methods used in particle therapy are also used in non-therapeutic fields. For example, these include research works for product development in the context of particle therapy which is performed on non-living phantoms or bodies, irradiation of materials, etc. For this purpose, loaded particles, for example, protons or carbon ions or other ions, are accelerated to high energies, formed into a particle beam and directed via high energy beam transport systems to one or several irradiation chambers. In one of these irradiation chambers the object with a target volume to be irradiated is irradiated with the particle beam.

In the process, it can occur that the target volume to be irradiated is moving. For example, when irradiating a patient breathing can result in the movement of the tumor to be irradiated. Such a movement can be simulated by means of model objects for research purposes called phantoms.

Especially when performing irradiation methods wherein a number of irradiation doses are to be successively deposited at different points in the target volume, it is difficult to achieve a desired homogeneous dose distribution in the target volume if the target volume moves during the process of irradiation.

On the one hand, methods are known wherein the target volume is irradiated merely at specific times when the target volume is located at a specific place or in a specific phase of movement. Such methods are known as gating methods. On the other hand, methods are known wherein the beam follows the movement of the target volume. Such methods are known by the term tracking method.

From U.S. Pat. Nos. 6,891,177, 6,710,362 B2 and US 2006/0033042 A1 methods and devices are known by means of which it is possible for the beam to follow the movement even in the direction of the beam.

It is the objective of the invention to provide a device for determining control parameters by means of which it is possible to design the tracking process of the beam in an advantageous manner. Furthermore, it is the objective of the invention to provide a respective method for determining beam parameters, an irradiation method comprising such beam parameters and a respective irradiation system.

This objective is achieved by means of the independent claims. Preferred embodiments of the invention are included in the dependent claims and are subsequently described in more detail. The preceding and the following description of the individual characteristics refers to the device category, as well as to the process category, without specifically mentioning it in each particular case. The individual characteristics disclosed in this way can also form a substantial part of the invention in combinations not shown in this context.

The invention-based device for determining control parameters for an irradiation system, by means of which a number of irradiation doses are successively deposited at different target points in a target volume, comprises:
an input device which is designed for detecting a target region and for detecting a movement of the target region,
an evaluation device for detecting control parameters for controlling a beam of the irradiation system in such a way that with the help of the control parameters a beam is able to follow the movement of the target region and to deposit a defined dose distribution in the target region,
wherein the evaluation device is designed in such a way that,
for determining the control parameters, at least a first selectable control parameter is determined so that the beam is able to follow the movement of the target region merely orthogonally to beam direction, or
for determining the control parameters, at least a first selectable control parameter and a further control parameter representing energy modulation are determined, wherein motion tracking in beam direction is taken into consideration.

The target region is the region to be irradiated, for example, a tumor. Preferably, the target volume comprises the target region and corresponds to the volume which is to be, or actually is, irradiated according to irradiation planning. In particular, the target volume can be larger than the target region and can comprise safety margins.

All in all, the device "determines" control parameters for the irradiation system. For example, this can be performed by indicating numerical tuples comprising relevant control parameters, each for different points in time. The correct irradiation process is, at least also, a function of the control parameters determined by the device. The evaluation unit "detects" control parameters, wherein the diction emphasizes that the evaluation unit is designed for "identifying" the control parameters, for example, by means of calculation. Of course, if necessary, the control parameters can also be detected to the extent that they are already determined in the sense described above. On the other hand, it is also possible to use different parts of the device than the evaluation unit for detection purposes. Consequently, the differentiation is more a linguistic matter than a technical matter. "Determining" emphasizes the result, whereas "detecting" focuses on the method of achieving the results.

A control parameter can be "selected" if it has not already been preset, for example, by the physical design of the irradiation system. If necessary, a user of the device can select the at least first control parameter so that the evaluation unit is able to detect the specifications of the respective control parameter. However, the selection can also be made by the evaluation unit itself, for example, by means of calculations or presettings.

When determining the control parameters mentioned above, motion tracking is taken into consideration. For example, this can be done by means of calculations which take motion tracking into consideration.

It has been recognized that the defined dose distribution to be applied can not only be achieved with a particular set of control parameters, but instead with many different sets of control parameters. Consequently, the control parameters comprise several degrees of freedom and when detecting the control parameters a selection is made; the number of possibly remaining degrees of freedom is reduced.

The determination of control parameters is performed by presetting boundary conditions for reducing the degrees of freedom. A first preset is represented by (previously) defined dose distribution to be deposited in the target region, possibly by taking into consideration structures to be protected (also known as OAR=organs at risk). This includes also that it is possible to tolerate small deviations from the preset dose distribution.

A further preset involves that the beam follows the moved target region at least in one direction, i.e., the dose application is made by using a tracking method. Preferably, the direction is arranged orthogonally to beam direction.

By way of contrast, in previously known methods an irradiation plan has been established for a reference situation. This reference situation is compared with the different movement phases and transformation rules are established between the reference situation and the movement phases. These transformation rules can then be applied to the irradiation plan. The required beam tracking, even in beam direction, is calculated by using these transformation rules.

To this end, it has been recognized that the performance of motion tracking of the beam in beam direction is usually considerably more complex than beam tracking in a direction running orthogonally to beam direction. While beam tracking can be performed in a comparatively simple manner with the help of scanner magnets, motion tracking requires energy modulation of the beam.

Therefore, the evaluation unit can now be designed in such a way that the detection of the control parameters is performed in that motion tracking of the beam merely occurs in a direction orthogonal to beam direction ("lateral tracking"). Consequently, the detection of at least one selectable control parameter takes place with the boundary condition or preset of using merely one motion tracking of the beam in a direction orthogonal to beam direction ("lateral tracking").

Alternatively, it is also possible to allow for motion tracking of the beam in beam direction, but to determine the control parameters in such a way that motion tracking of the beam in beam direction is taken into consideration. In the process, not only the control parameter representing the energy modulation of the beam, i.e., the parameter indicating beam tracking in beam direction is determined taking into consideration motion tracking of the beam in beam direction. At least one different control parameter, preferably a control parameter which does not concern the energy of the beam, is also determined taking into consideration motion tracking of the beam in beam direction. For example, these control parameters concern the beam entry direction, the number of regions of irradiation, the weighting of the regions among each other, the focal size of the particle beam, an overlap of individual target doses, timing the time of application with the movement of the target volume, the scan path, the scan speed, a possible longitudinal expansion of the beam, the number of irradiation sessions, a possible number of irradiation cycles per irradiation session, several partial regions of the target volume and other control parameters which are described below. As shown by these examples, respective control parameters do not have to have a direct effect on the lateral deflection, i.e., lateral scanning or lateral tracking.

All in all, it can be viewed in this way that when determining control parameters boundary conditions comprise also such boundary conditions which concern motion tracking of the beam in beam direction. The control parameters for beam tracking in beam direction are not merely subsequently calculated, beam tracking in beam direction is included from the start in the determination of the control parameters, even for at least one selectable control parameter which is not directly associated with the energy modulation of the beam or with beam tracking in lateral direction.

The possibility of freely selecting a control parameter indicates that this control parameter is not preset as a fixed parameter when detecting the control parameters. Instead, this control parameter, possibly within specific predetermined limits, is variable and is set when the control parameters are determined.

The objective of reducing the extent of motion tracking in beam direction can be achieved by considering motion tracking in beam direction when detecting the at least one selectable control parameter; or, alternatively, by allowing merely one lateral tracking, i.e., tracking in beam direction, when detecting the control parameters. In the latter case, motion tracking of the beam in beam direction is considered "implicitly", so to speak because such beam tracking is not allowed. A respective arrangement can already be preset by means of a mechanical design of the system and/or the device.

In both cases, it is possible, to set the at least one selectable parameter in such a way that the more complex beam tracking in beam direction is considered and optimized, in particular minimized. This means that the requirement or the extent of beam tracking in beam direction is lower than in traditional irradiation planning, it is actually reduced.

At the same time, the target region can be detected with the help of an image data record in which the image data is represented. For example, by means of a CT data record, the target region can be determined automatically and/or in interaction with the user. In the same way, it is possible to determine further target regions which should be protected during subsequent irradiation, i.e., they have to be exposed to the lowest possible dose, or a dose that has to be lower than a limit value (the so-called OAR; "organs at risk"). In this way, it is possible to detect an intended dose distribution which indicates how to apply an irradiation dose to the target object. Furthermore, in order to deposit this intended dose distribution, control parameters are detected.

In the process, the control parameters must not necessarily be direct control parameters, i.e., control parameters which can be used directly, without interpretation or calculation steps for controlling the system. An irradiation plan which was developed in the context of irradiation planning can also represent a data record of control parameters which can be used for controlling the system in order to determine the control parameters. The irradiation system is then able to load an irradiation plan and the irradiation plan can be used to control the irradiation system according to presettings stored in the irradiation plan.

The control parameters which are determined in a first phase during irradiation planning can form a complete set of control parameters. This means that the complete set of control parameters is sufficient to control an irradiation system for irradiating the target region with the tracking method, especially during the entire period of irradiation. Completeness concerns the number of determined control parameters per relevant point in time, as well as the number of intervals for which a respective control parameter was determined.

However, this is not absolutely necessary. The control parameters which are determined in the first phase can still be incomplete. This means that the incomplete set of control parameters has been stored for irradiating the target region with the tracking method. However, the incomplete set is completed in a second phase by means of further control parameters, which then results in a complete set of control parameters. In this way, it is possible, if necessary, to detect parameters not previously detected, for example, the focal spot or focus of the beam, or with regard to parameters already detected or their value at other points in time. In this way, it is possible, for example, to implement in a simple manner computation-intensive calculations in a first phase in the context of irradiation planning while in the second phase, which takes place immediately before or even during irradiation, the actual situation can be considered. This allows for iterative tracking of control parameters during irradiation, so to speak.

The movement of the target region can also be detected in different manners. For example, the movement of the target region can be detected from a data set wherein the movement of the target region is depicted, for example, in a 4D CT data set.

In a preferred embodiment, the movement can be determined with the help of imaging methods even at the treatment site, immediately prior to irradiation. Furthermore, the movement can be detected during an irradiation process and can be used to adapt or complete control parameters for controlling the irradiation system.

However, it is also possible to use an anticipated movement typical for the target region. For example, when the target region is a lung, it can be sufficient, depending on the required accuracy and regularity of the movement, to use movements typical for breathing as movement of the target volume. In general, the movement does not have to be explicitly indicated (for example, as amplitude over time). It can be sufficient to use parameters which can be derived from the explicit movement, for example, coverage probabilities.

Furthermore, it is possible to derive indirectly the movement of the target region due to other movements. For example, it is possible to determine the movement of the target region by means of movements on the body surface, or to determine the movement of the target region by means of the movement of other internal structures.

Besides the movement of the target region it is also possible to detect other clinically relevant regions, for example, the movement of an organ to be protected.

In an advantageous manner, the evaluation unit is designed in such a way that the control parameters are detected in such a way that the beam follows the movement of the target object in at least two different directions.

In this way it is possible to track the beam in a plane perpendicular to the beam extending direction or even in all three spatial dimensions.

In a particular embodiment, the evaluation unit is designed in such a way that a measure is determined and used for detecting the control parameters, which measure considers the motion tracking to be performed in beam direction.

Such a measure makes it easy to take into consideration motion tracking in beam direction when determining control parameters. For example, the measure can be incorporated in a target function which is optimized, or minimized. The measure which describes the tracking process in beam direction is incorporated in the target function in such a way that specific motion tracking processes, for example, a great extent of motion tracking, is taken into consideration to a greater or lesser extent than a small extent of motion tracking which in the sense of the invention is described as "penalized."

However, considering motion tracking in beam direction with the help of the measure, by means of which the extent of motion tracking can be recorded as a continuous value, is only one form of consideration. For example, it is also possible to predetermine a boundary condition which limits the maximum extent to which motion tracking in beam direction can take place, or discretizes it to the preset values or values to be optimized.

For example, in this way it is possible to limit the exposure of a beam tracking system which takes place when performing motion tracking.

If a scanning process is used, beam parameters which, for example, are optimized with the help of a target function can involve the energy E of a beam, the focus F of the beam, the position x, y of the beam in a plane perpendicular to beam direction, the number of particles N in a rasterpoint, the change of beam position resulting from the motion tracking of the beam dx, dy, dz in all three spatial directions, the scan path, the scan speed (extracted fluence) and/or the change of the number of particles dN. At the same time, it is possible to predetermine beam parameters for each rasterpoint.

For example, the measure can take into consideration amplitude of motion tracking of the beam in beam direction, a speed of motion tracking of the beam in beam direction, and/or a variation of the speed of motion tracking of the beam in beam direction.

At the same time, the measure can consider the amplitude, speed and/or variation of speed used from rasterpoint to rasterpoint for each individual rasterpoint. However, it is also possible to use as a measure the maximum, medium or minimal values occurring in a movement cycle which makes it easier to implement optimization. Possibly the measure does not have to be evaluated frequently.

In a simple case, it is possible to use as measure the required changes of the beam range $\delta z$ which are included the target function of optimization, and to include them in such a way that large $\delta z$ values are penalized.

For example, when the measure indicates the sequence of changes of the $\delta z$ values over time, particularly "fast" changes of the $\delta z$ values can be penalized because they place particularly high demands on the energy modulation system.

However, the measure can also describe a further parameter which can be derived from the $\delta z$ values, for example, a resulting requirement for the energy modulation system.

The measure can also serve the purpose of determining a termination criterion for irradiation in order to interrupt or stop irradiation when the movement shows extreme values that exclude safe irradiation.

In a particular embodiment, the evaluation unit is designed in such a way that the at least one first control parameter determines at least one movement phase during which at least a first part of the target points is not approached.

In this embodiment, it is now possible to allow as additional degree of freedom at least one movement phase. For example, with this (selectable) movement phase/phases, it is possible to exclude that during a particular phase a part of the target points is approached that would require a great extent of beam tracking in beam direction because in this movement phase the target region moves especially fast. The first part of the target points can also comprise all target points. In this case, irradiation is combined with a Gating method.

In a further embodiment, the evaluation unit is designed in such a way that a first control parameter determines at least a second part of the target points which is not approached by using motion tracking of the beam.

In this embodiment, it can be allowed as a degree of freedom to specify that a part of the target points is specified which is not "tracked." For example, by specifying the target points that are not approached using motion tracking of the beam, it can be determined that no motion tracking is performed for certain especially critical target points. For example, distal layers which are accountable for a good portion of the dose of the target region can only be irradiated with a Gating method without tracking. In this way dosimetry can be guaranteed. The remaining area in which altogether a comparatively lower dose is directly deposited can then be irradiated merely with lateral tracking. This can still be sufficient for depositing the desired dose distribution with adequate accuracy, even if no motion tracking in beam direction is performed. The described characteristic of the method also aims at an optimization of the irradiation parameters which concerns individual areas of the target volume.

In a different embodiment, the evaluation unit is designed in such a way that by means of the at least one first control parameter it is possible to determine a repeated approach of the rasterpoints and/or a succession of the approach of the target points.

In this embodiment, it can be allowed as a degree of freedom that target points are approached repeatedly, i.e., so-called rescanning is performed, or the beam path, which is the sequence of approach of the target points, can be arranged in variable manner.

For example, without rescanning it is not possible to achieve certain homogeneity of dose distribution and to fulfill specific presets with regard to tracking in beam direction because rescanning facilitates homogeneity of irradiation by means of averaging effects. However when rescanning is allowed as a degree of freedom, it becomes possible to achieve homogeneity of dose distribution and at the same time fulfill specific presets with regard to tracking in beam direction. The same applies to the beam path. When a specific beam path does not allow fulfilling a preset with regard to tracking in beam direction, a change of the beam path can already be sufficient to fulfill the preset.

In a further embodiment, the evaluation unit is designed in such a way that by means of the at least one first control parameter it is possible to determine spatial orientation of a beam inbound direction, a number of beam inbound directions and/or an overlap of rasterpoints.

These parameters can also be incorporated as degrees of freedom in the determination of control parameters. For example, a change in beam inbound direction can already be sufficient to fulfill a specific preset with regard to tracking in beam direction. This can also be achieved by distributing the dose to different areas which can be weighted differently. A desired homogeneity of the dose can be restored in consideration of the preset even by changing the overlap of the target points in lateral and longitudinal direction. An overlap is represented by the distance of the target points to each other and the size of focus of the beam when irradiating the target points.

It is also possible to select one or several beam inbound directions. These beam directions indicate from which direction, with respect to the target object, the particle beam is directed on the target object. For example, in a system this can be implemented in such a way that the target object is positioned in relation to the beam, and/or that the spatial orientation of the beam is adjusted, for example, via a respective position of a Gantry.

An invention-based irradiation system, especially a particle therapy device, comprises a device for determining control parameters according to any one of claims 1 to 9.

In this way, it is possible to design an energy modulation system, which is used for motion tracking of a beam in beam direction, in a simpler and more cost-effective manner or to use the system even without an energy modulation system. By determining the control parameters, it is possible to consider presets with regard to a requirement for the energy modulation system or for tracking in beam direction, which is not used in merely lateral tracking.

The invention-based method for determining control parameters for an irradiation system, by means of which a number of irradiation doses can be deposited successively at different target points within a target volume, comprises the following steps:

Detecting a target region with an input device, detecting a movement of the target region with the input device, determining control parameters for controlling a beam of the irradiation system with an evaluation unit in such a way that by means of the control parameters the beam can follow the movement of the target region and a defined dose distribution can be deposited in the target region, wherein, when the evaluation unit determines the control parameters, at least a first selectable control parameter is determined in such a way that the beam follows the movement of the target region merely orthogonally to beam direction, or wherein, when the evaluation unit determines the control parameters, at least a first selectable control parameter and a further control parameter which represents an energy modulation of the beam, are detected, and wherein motion tracking in beam direction is taken into consideration.

The further control parameter which represents an energy modulation of the beam in beam direction is directly associated with beam tracking in beam direction. It is therefore necessary that the further control parameter is determined by taking into consideration motion tracking in beam direction. However, a different control parameter, the first selectable control parameter, is also determined by taking into consideration motion tracking in beam direction. This control parameter does not have to be directly associated with the energy modulation of the beam which is required for motion tracking of the beam in beam direction. In other words, this control parameter has an effect on at least one aspect of irradiation being independent of energy modulation. Furthermore, as previously described, it is not necessary that this first selectable control parameter has a direct effect on the lateral deflection of the beam. For example, it can have an effect on the rotation of the Gantry. In particular, it can be independent of lateral scanning and lateral tracking.

The same applies to the first selectable control parameter, which is determined in such a way that the beam follows the movement of the target region merely orthogonally to beam direction. Even this parameter does not have to be directly associated with beam tracking in orthogonal direction or lateral scanning. In other words, this control parameter can have an effect on an aspect of irradiation that is independent of beam tracking in orthogonal direction or lateral scanning.

Furthermore, the invention concerns a method for irradiating a moved target region with a set of control parameters for controlling an irradiation device, which control parameters are determined according to the method described above.

In particular, it is possible with this method of irradiation to irradiate a target region which is part of a non-living body, for example, within a phantom used for testing irradiation planning, for research purposes, for example, of cell cultures.

In principle, the invention concerns also a device for determining control parameters for an irradiation system by means of which a number of irradiation doses are deposited successively at different target points in a target volume, which device comprises:

an input device which is designed for detecting a target region and for detecting a movement of the target region, an evaluation device for determining control parameters for controlling a beam of the irradiation system in such a way that with the help of the control parameters a beam is able to follow the movement of the target region and to deposit a defined dose distribution in the target region, wherein the evaluation device is designed in such a way that, for detecting the control parameters, at least a first selectable control parameter and a further control parameter representing an energy modulation of the beam are detected, wherein motion tracking in beam direction is taken into consideration in that the energy modulation of the beam is suppressed and the beam can follow the movement of the target region merely orthogonally to beam direction.

Figure 2:
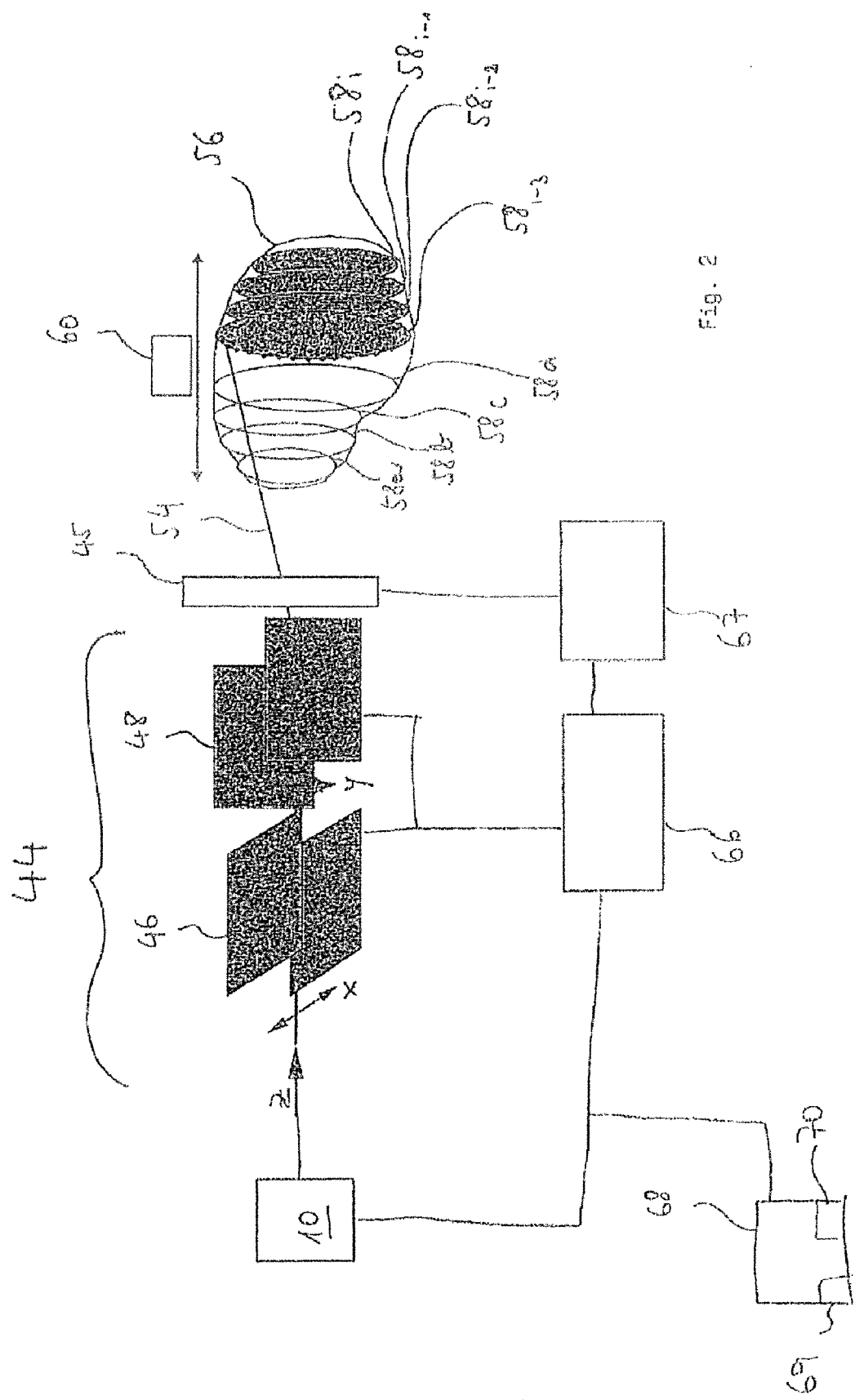
Figure 3:
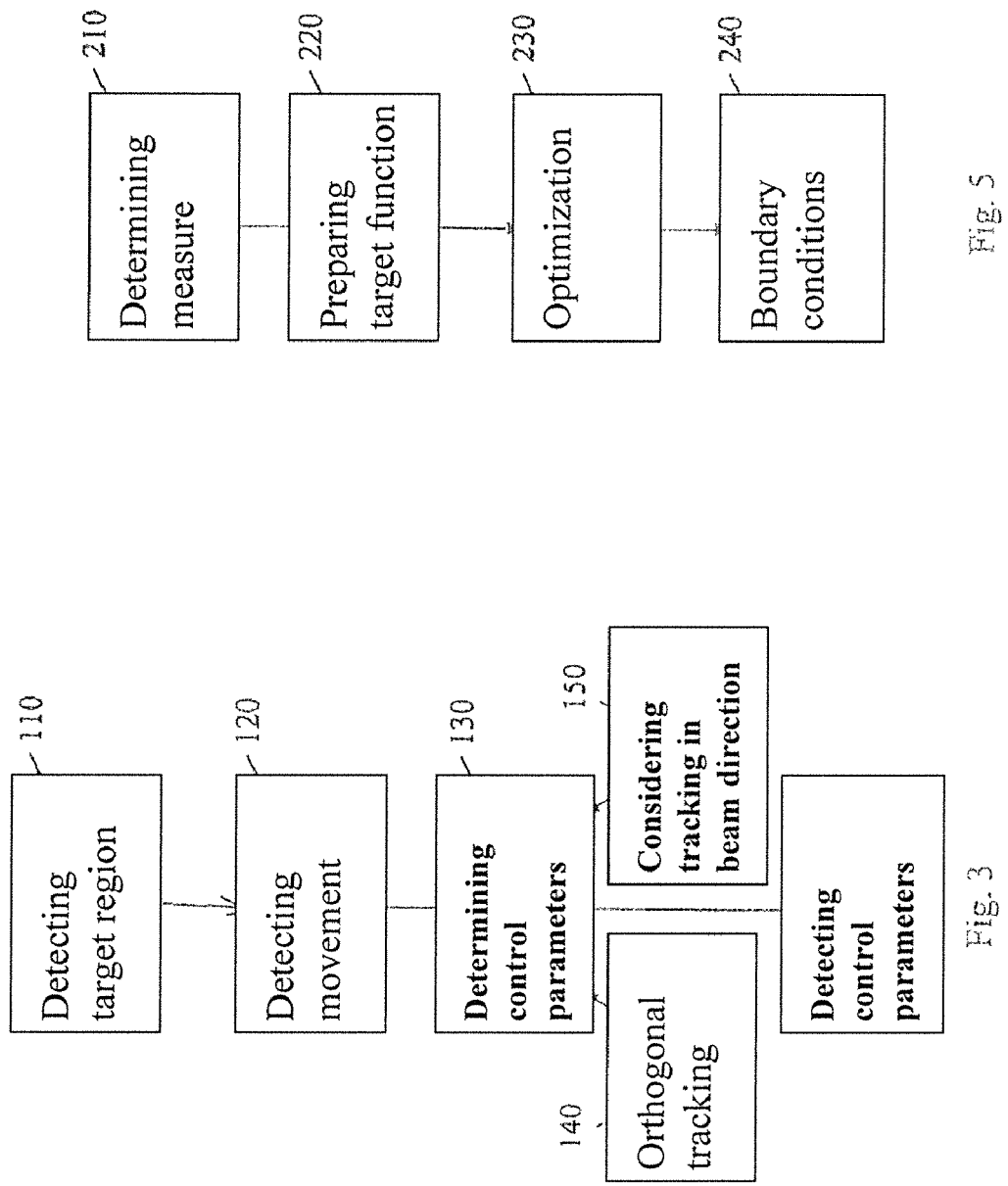

By means of the following drawing, the embodiments of the invention including practical developments according to the characteristics of the dependent claims are described in more detail, without being restricted to these characteristics. It is shown in:

FIG. 1 a schematic overview of the structure of a particle therapy device,

FIG. 2 a diagram of a target volume to be irradiated by means of a grid scanning device, FIG. 3 a flow diagram of a method for determining control parameters for the irradiation system shown in FIG. 1, FIG. 4 an overview of different control parameters, which are detected by taking into consideration movement tracking of the beam in beam direction, and FIG. 5 a flow diagram for determining control parameters with the help of a target function.

FIG. 1 shows in a schematic depiction a diagram of the structure of a particle therapy device 10. The particle therapy device 10 is used for irradiating a body 14 arranged on a positioning device 12 with a beam of particles 16, which is subsequently called a particle beam 16. In particular, the tumorous tissue of a patient is irradiated with the particle beam. Provision has also been made to use the particle beam device 10 for irradiating a non-living body 18, in particular a water phantom 18. For example, the irradiation of the water phantom 18 takes place for purposes of testing and verifying irradiation parameters before and/or after a patient 14 has been irradiated. Moreover, provision has been made to irradiate with the particle beam 16 other bodies, in particular experimental setups, for example, cell cultures or bacterial cultures for research purposes. In all cases, this can involve moved or resting bodies 14, 18.

The particles used primarily involve particles such as protons, pions, helium ions, carbon ions or ions of other elements. Usually, such particles are generated in a particle source 20, which is subsequently called ion source 20. When, as shown in FIG. 1, the particle beam device 10 comprises two particle sources, for example, two ion sources 20 and 20', a switching magnet 24 is arranged between the ion sources 20 and 20' and a pre-accelerator 22. By means of the switching magnet 24, the beam generated by the ion source 20, as well as the beam generated by the ion source 20' can be supplied in the pre-accelerator 22, wherein the ion beam from the ion source 20 and the ion source 20' can be supplied alternately within a short time interval. The ion sources 20 and 20' are used alternately. In this way it is possible to use in the particle therapy device 10 alternately or within a short time interval successively particle beams with two different types of ion. For example, particle beams with protons and with carbon ions can be operated almost simultaneously by switching in extremely short time intervals between the ion source 20 and 20'. For example, in this case, the ion source 20 generates a proton beam and the ion source 20' generates a carbon ion beam.

The ion beam or particle beam generated (and, if required, selected by means of the switching magnet 24) by the, or one of the, ion sources 20, 20' is accelerated in the pre-accelerator 22 to a first energy level. For example, the pre-accelerator 22 is a linear accelerator (LINAC). Subsequently, the particles are supplied in a further accelerator 26, for example, a circular accelerator, especially a synchrotron or cyclotron. In the accelerator 26, the particle beam is accelerated to at least an energy level required for irradiating a target volume (not shown) assigned in a body 18. After the particle beam has left the accelerator 26, a high-energy beam transport system 28 transports the particle beam into one or several irradiation chambers 30, 30', 30'', where the positioning device 12, for example, a patient bed, with the patient 14 or the phantom 18 for verifying irradiation planning, is located. In the irradiation chamber 30 or 30', irradiation of the body 14, 18 is performed from a fixed direction, and the body 14, 18 is in a spatially fixed position. These irradiation chambers 30, 30' are called "fixed-beam" chambers. In the treatment room 30'' a Gantry 34 is provided which can preferably be rotated and which can be swiveled about an axis 32. By means of the Gantry 34, the body 14 to be irradiated or the phantom 18 can be irradiated from different directions. For this purpose, the particle beam is swiveled about the body 14, 18 to be irradiated by means of a Gantry beam-guide system 36 located in the Gantry 34. FIG. 1 shows a first position 38 and a second position 38' in representation of different positions of the Gantry beam-guide system 36 of the Gantry 34. It is certainly also possible to use for the Gantry beam-guide system 36 (not shown for reasons of clarity) intermediate positions on at least one semi-sphere above the body 14, 18 to be irradiated in an imaginary sphere around the body 14, 18 to be irradiated. As a result, the target volume to be irradiated can be irradiated perpendicular to the axis 32 from several directions.

In the irradiation chamber 30, 30', the particle beam comes out of an end of a vacuum system of the high-energy beam transport system 28 called beam outlet 40, 40' and impinges the target volume (not shown) in the body 14 or 18 to be irradiated. Usually, the target volume is located in an iso-center 42, 42' of the respective irradiation chamber.

The basic structure of a particle therapy device 10, as the one shown in FIG. 1, is exemplary for particle therapy devices, but can also have different structures.

The subsequently described embodiments can be used with the particle therapy device shown in FIG. 1, as well as with other particle therapy devices.

FIG. 2 shows a diagram of devices which can be used for irradiation in the sense of the invention. In particular, FIG. 2 shows a grid scanning device 44 and an energy modulation system 45.

In this context, the same reference numerals depict the same objects. The grid scanning device 44 comprises a first particle beam deflection device 46 and a second particle beam deflection device 48 which, in particular, can comprise magnets. The two particle beam deflection devices 46, 48 can deflect the beam in horizontal or vertical direction. Arrow 50 shows the deflection direction of a particle beam 54 in x direction (horizontal) and arrow 52 shows the deflection of the particle beam 54 in y direction (vertical). Consequently, by means of the grid scanning device 44, the particle beam 54 is able to scan or skim a matrix consisting of points with the positions $(x_j, y_j)$, wherein i represents the number of points of the matrix to be scanned. These points $(x_j, y_j)$ are described as rasterpoints. The target volume 56 in the body 14 or 18 to be irradiated is composed of iso-energy discs or layers 58$a$, 58$b$, 58$c$, ... 58$i$, each having different fields of rasterpoints $(x_j, y_j)$. To this end, the iso-energy layers 58$a$, 58$b$, 58$c$, ... 58$i$ are each assigned to a specific position on the z axis.

In the example shown, the counting of the layers begins with 58$a$ on the side facing the grid scanning device 44, while the layer (distal layer) furthest afar from the grid scanning device 44 is described with 58$i$, wherein i shows the number of layers. To adjust the particle beam 54 to a respective layer 58$a$, 58$b$, 58$c$, ... 58$i$, the particle beam 54 has a different energy level, respectively. For this purpose, the particle beam 54 with the lowest energy level is deposited in the disc 58$a$ and the particle beam 54 with the highest energy level is deposited in the disc 58$i$.

Consequently, irradiation using a scanning method comprises a particle beam 54 which is dimensioned in such a way that it is possible to deposit only a single dose at a small localized area in the target volume 56. As a result, this small area can be assigned to a rasterpoint, wherein the parameters of the rasterpoints, i.e., the coordinates of the rasterpoints and/or the parameters of the particle beam that are adjusted to the coordinates of the rasterpoints, are preferably included in irradiation planning.

In order to irradiate the entire target volume 56, different rasterpoints which are sites of the target volume 56 are successively irradiated, one after another. The particle beam 54 is deflected with the help of scanning magnets 46 and 48 and scanned across the target volume, thus scanning or sampling the rasterpoints. In order to irradiate different iso-energy layers, the energy of the particle beam 54 is adjusted appropriately. A target volume is shown in which three distal iso-energy layers $58_i$, $58_{i-1}$, $58_{i-2}$ have already been irradiated and in which the particle beam scans across the subsequent iso-energy layer $58_{i-3}$.

Different scanning methods are known, for example, grid scanning wherein the beam scans without stopping between adjacent rasterpoints across the target volume, spot scanning wherein shutoff between target points takes place, or a continuous scanning method wherein the beam is continuously deflected.

If required, an additional energy modulation system 45 can be provided. For example, this device can be arranged between the scanning magnets 46, 48 and the target volume 56, wherein it is possible with the help of this device to readjust the depth of penetration of the particle beam 54 to a movement of the target volume 56. For example, the energy modulation system can be designed in the way described in the publications U.S. Pat. Nos. 6,891,177 B1, 6,710,362 B2, or US 2006/0033042 A1.

In addition and/or alternatively, it is possible to provide an energy modulation system located in front of the scanning magnet, viewed in beam direction, which energy modulation system is designed for motion tracking of the particle beam in beam direction. This energy modulation system can be designed as a separate unit analogous to 45 or can represent a characteristic of the accelerator. In the latter case, the accelerator is able to change the beam energy in time intervals which correspond to the irradiation time of a rasterpoint.

An energy modulation system 45 can also be used for so-called depth scanning. This means that not the layers are irradiated successively, but the scan path can run also between the layers.

However, it is not necessary to have available such an energy modulation system 45 which allows for motion tracking in beam direction. In this case, irradiation planning or the detection of control parameters is designed in such a way that irradiation of the moved target volume 56 is performed merely with motion tracking in a direction orthogonal to beam direction.

Alternatively and/or additionally, it is possible to use an energy modulation system arranged in front of the scanning magnets 46, 48 viewed in beam direction 16, which energy modulation system adjusts, respectively, the energy levels of the particle beam 54 for the different iso-energy layers. The latter method is especially used in particle beam devices having a cyclotron.

Consequently, the scanning process results in temporally protracted irradiation during which the dose to be deposited is incrementally deposited. This dose generates an incrementally growing activity distribution.

For example, the position of the particle beam 54 in the target volume 56 can be examined by means of a positron emission tomography device (PET). The PET device comprises at least two detectors and a control device which are actively connected with the control device of the grid scanning device 44. In this way, data recording with the PET device and the irradiation process can be matched to each other.

Before irradiating a target volume 56, irradiation planning is performed in order to control irradiation according to the prepared irradiation planning, i.e., the scanning of the target volume 56 with the particle beam 54. Irradiation planning represents the determination of control parameters for controlling the irradiation device 10. Irradiation planning is performed with an irradiation planning device 68 especially designed for this purpose.

To this end, a computer tomograph or nuclear magnetic resonance or other diagnostic devices are used to detect the position and expansion of a tumor to be irradiated or any other target volume 56.

Besides the position and expansion of a target volume 56 to be irradiated, it is also possible to detect the movement of the target volume 56 and, if required, other clinically relevant target volumes. Different ways can be used to achieve this goal. On the one hand, imaging modality can be designed in such a way that the movement of the target volume can be detected by means of the imaging process, for example, in a 4D computer tomography. The movement of the target volume 56 can be detected with the help of a motion detection device 60.

Different motion detection devices 60 can be used: for example, the movement of the abdominal wall can be detected by means of a camera system with the help of measurements of the movement amplitude of an infrared marker. It is also possible to detect the movement phase from the expansion of a sensor strapped around the abdomen or chest. When using the method of spirometry, the patient breathes through a volume sensor by means of which it is possible to detect temporally resolved the volume of the inhaled and exhaled air. It is also possible to provide a temperature sensor which can provide information about the breathing process. Motion detection can also be achieved with the help of an especially small, electromagnetic transponder the size of a grain of rice which is implanted in the target volume. It is also possible to use external imaging systems, for example ultrasound or fluoroscopy for monitoring the movement of the target volume, wherein, for example, implanted markers can be used to support the detection of movements by detecting them with the imaging system. In principle, it is also possible to use systems which allow for volumetric imaging.

Depending on the regularity of the movement to be expected, it can be sufficient to indicate the anticipated movement of the target volume 56. In this case, the anticipated movement indicates the actual movement of the target volume 56. It is not necessary to specifically monitor the movement of the target volume 56 in relation to the actual movement.

The data of the imaging system are immediately, or after processing through further devices (not shown), supplied to the irradiation planning device 68 by means of an input device 69 of the irradiation planning device 68. The irradiation planning device 68 prepares a data record which includes the control parameters used for controlling the irradiation system according to specific presets. For example, the irradiation planning device 68 can be a workplace computer, a workstation or a different computer. By means of its user interface, software or other characteristics, the irradiation planning device 68 is usually designed in such a way that a user defines with the device 68 the target volume(s), the dose distribution to be applied, its distribution to several sessions, the direction of irradiation and other details involving irradiation planning.

The irradiation planning device 68 comprises an evaluation unit 70 for processing the input and is designed in such a way that the detection of control parameters can be performed with a method that is subsequently described in more detail by means of FIG. 3 and FIG. 4.

The control parameters are transferred to the irradiation device 10. The irradiation device 10 is controlled by a control system which comprises individual subordinate control devices for different subsystems. For example, this includes the control device 66 for the grid scanning device 44, if required, a control device 67 for the energy modulation system and other additional control devices for other parts of the irradiation device 10, which are not shown for reasons of clear arrangement. Furthermore, the control system comprises diagnostic devices (which are also not shown for reasons of clear arrangement), by means of which the condition of the different parts of the irradiation device 10 can be monitored. At the same time, the control system controls the course of irradiation according to the detected control parameters.

FIG. 3 shows the invention-based method in the form of a flow chart. The method serves the purpose of determining control parameters for an irradiation device 10 in which a number of irradiation doses are successively applied to different target points in a target volume 56.

In procedural step 110, a target region or target volume 56 is detected. In procedural step 120, the movement of the target region or the target volume 56 is detected, for example, with the help of a 4D CT data record. The detection of the target region/volume can comprise also the detection of further, clinically relevant regions, for example organs to be protected (OAR=organs at risk).

In procedural step 130, control parameters for controlling a beam are detected in such a way that by means of the control parameters the beam can follow the movement of the target region, and in the target region a dose distribution can be deposited that has been predefined, for example, by a user. In this procedural step 130, the set of control parameters by means of which subsequent irradiation is performed is not necessarily determined completely. This means that in procedural step 130 it is possible to determine merely part of the control parameters which can be later completed with further control parameters which then form together a complete set for controlling the irradiation device. If required, the set for controlling the irradiation device can be completed even online, i.e., during the process of irradiating the target volume 56.

Here, in an alternative variation of an embodiment, in step 140, when detecting the control parameters, at least a first selectable control parameter is determined in such a way that the beam follows the movement of the target region or target volume 56 merely orthogonally to the beam direction.

This control parameter can be selected from a number of parameters which characterize irradiation. This control parameter describes a parameter which is not directly connected with motion tracking. Control parameters which fall into this category are described in more detail by means of FIG. 4.

If it becomes apparent when detecting the control parameters that even when this control parameter is freely selected it is not possible to fulfill the preset of merely performing orthogonal tracking and, at the same time, fulfilling the other presets, for example, the deposition of intended dose distribution with sufficient quality, one or several further control parameters can be set to be selectable. By thus providing additional degrees of freedom, it is possible to fulfill the presets concerning intended dose distribution and merely orthogonal tracking.

Alternatively, in step 150, when determining the control parameters, at least a first selectable control parameter and a further control parameter, which represents an energy modulation of the beam, is detected wherein the at least first control parameter and the further control parameter are detected in consideration of motion tracking in beam direction.

Consequently, in this embodiment, motion tracking in beam direction is allowed. However, not only the further control parameter, which represents an energy modulation of the beam and thus is directly connected with motion tracking in beam direction, is determined in consideration of motion tracking in beam direction, but also the first selectable control parameter. As described in procedural step 140, this control parameter can be selected from a number of parameters characterizing irradiation. The first selectable control parameter describes a parameter which is not directly connected with motion tracking. Control parameters which fall into this category are described in more detail by means of FIG. 4.

This embodiment allows taking into consideration target values regarding motion tracking in beam direction. For example, it is possible to draw an upper limit which describes the extent of motion tracking in beam direction and which should not be exceeded. For example, it is possible to optimize the first selectable control parameter and the further control parameter in such a way that the motion tracking occurring in beam direction is reduced, even minimized, with regard to the maximum required tracking or the required tracking changes.

If it becomes apparent when detecting the control parameters that even when this first selectable control parameter is freely selected it is not possible to fulfill the preset, to maintain a target value with regard to beam tracking in beam direction and, at the same time, fulfill all other target values, for example, the deposition of intended dose distribution with sufficient quality, one or several further control parameters can be set to be selectable. By thus providing additional degrees of freedom, it is possible to fulfill the presets concerning intended dose distribution and motion tracking in beam direction.

Alternatively, the control parameters detected in steps 140 and 150 are supplied to step 130 as input data. In this way, a record of control parameters is prepared which can be used, if desired, for controlling a course of irradiation in procedural step 160.

In one embodiment of the method, it is possible, in step 160, to irradiate a moved target region wherein the target region comprises at least a section of a non-living body, in particular, a phantom.

FIG. 4 shows a list of control parameters which are not directly connected with motion tracking. However, in the context of irradiation planning, they may be selected in such a way that it is possible to fulfill a preset which concerns motion tracking in target direction.

Beam Inbound Direction:

By appropriately selecting the beam inbound direction, it is possible to maintain target values which concern motion tracking in beam direction and still deposit an intended dose distribution in sufficient quality.

Number of Regions:

The same applies when the number of areas is not preset by default but, instead, can be selected during the process of irradiation planning. An area is defined by a beam inbound direction. When the number of areas is increased, i.e., when the intended dose distribution is divided in many areas with different beam inbound directions, it is easier to maintain target values. At the same time, it is possible to consider the areas individually and/or parallel, i.e., the control parameters for the individual areas can be detected, and especially optimized, separately or mutually.

Overlap of Individual Rasterpoints:

For example, a minor overlap requires precise motion tracking. In a larger overlap, an intended dose can be deposited even when the tracking process is not performed in a precise manner, because it is necessary to consider a specific preset which restricts motion tracking of the beam in beam direction. The disadvantage of a larger overlap is that the steepness of decline in dose distribution at the margins becomes less. However, depending on the structure surrounding the target volume, this can be tolerable.

Rescanning:

The process of rescanning involves that a rasterpoint is approached several times until a desired dose is deposited at the rasterpoint. Rescanning often results in the fact that undesired effects are correctively averaged which would have existed without rescanning. For example, without rescanning it is not possible to deposit an intended dose distribution and, at the same time, fulfill a specific preset regarding tracking in beam direction. However, if, as a degree of freedom, rescanning is allowed, it is possible to fulfill both presets. In the process, it is possible to determine a selectable parameter, to decide how often a rasterpoint should be approached, etc.

Adjusting the Scan Path:

When the scan path is preset by default, i.e., the sequence in which the rasterpoints should be scanned has been set, it can result in the fact that it is not possible to maintain a specific preset regarding motion tracking in beam direction. By changing the scan path, it now becomes possible to maintain a preset regarding motion tracking in beam direction.

In particular, it is possible to allow three-dimensional scan paths. As a result, it is no longer required to irradiate successively iso-energy layer after iso-energy layer, but it is possible to switch between the iso-energy layers before the irradiation process of a particular iso-energy layer is concluded. For example, this involves that the iso-energy layers no longer have to be irradiated successively but, instead, it is possible to irradiate first the even iso-energy layers and then all uneven iso-energy layers, or the like.

Adjusting the Scan Speed:

When the scan speed, which has been determined for the extracted number of particles per time unit or beam pulse, is preset by default, it can result in the fact that the speed of the compensation system and/or the change in speed of the compensation system is not sufficient to track the beam. When the scan speed is a freely selectable parameter, the requirement for the compensation system can be reduced, especially by reducing the scan speed. For example, when the scan speed is increased, it is possible to increase the number of rasterpoints which can be irradiated successively without changing possibly required longitudinal motion tracking. The change of scan speed can be performed globally per irradiation process, per beam pulse, or even for at least one rasterpoint.

Parameters Describing a Combination of Different Types of Motion Management:

Combinations of Gating and Tracking:

When identifying rasterpoints in which it is not possible to maintain a specific preset regarding motion tracking in beam direction, a time slot can be determined during which the rasterpoints should not be irradiated. As a result, it is possible to define that these rasterpoints are irradiated only when the movement of the target volume is less distinct. In this way, it is again possible to fulfill a preset regarding motion tracking in beam direction. Consequently, these rasterpoints have been introduced to a Gating process. In the same way, it is possible for specific rasterpoints which are especially important for the dose deposition to apply the dose with the Gating method, while for rasterpoints which play a subordinate role for the dose deposition a tracking process is allowed, merely orthogonally or even in beam direction with specific presets.

Combinations Consisting of Orthogonal Tracking and Tracking in Beam Direction:

When identifying rasterpoints in which it is not possible to achieve an intended dose distribution by merely performing a tracking process in orthogonal direction, these rasterpoints can be approved for tracking in z direction.

FIG. 5 shows a diagram of the procedural steps which are performed in determining the selectable control parameters which were described in more detail in FIG. 4.

In a first step, a measure can be determined which considers motion tracking in beam direction (procedural step 210).

This measure takes into consideration the specification of the control parameters which occur in motion tracking to be performed in beam direction. For example, the measure can be characterized by amplitude of motion tracking of the beam in beam direction, speed of motion tracking of the beam in beam direction, and/or variation of the speed of motion tracking of the beam in beam direction.

Determining the measure offers a simple possibility of considering motion tracking in beam direction when determining the control parameters.

For example, it is possible to provide a target function which incorporates the measure (procedural step 220).

Subsequently, the control parameters are optimized on the basis of the target function (procedural step 230). This optimization can be performed by considering boundary conditions which reflect the presets placed on irradiation planning (procedural step 240).

Subsequently, a formula is shown as an example which describes the target function to be optimized.

A target volume to be irradiated is defined in a target region. For example, this can be done with the help of a CT data record. The target function is based on this target region or target volume.

It is possible to describe the target region by means of a number of voxels M'. The index k indicates the individual voxels k=1 . . . M'. In the target region, an intended dose $D_{pre}^{k}$ can be preset.

It is possible to describe the target volume in the target region by means of a number M of rasterpoints which are approached successively. The rasterpoints are indicated with i, i=1 . . . M.

It is possible to describe the movement of the target volume by means of a number L of 4D CT phases, i.e., by means of a four-dimensional CT image in which the movement is represented. The individual phases are indicated with the index j, j=1 . . . L.

In the target function, the number of particles per rasterpoint are included as parameters to be optimized $\vec{N}=(N_1, N_2, \ldots N_M)$, the fluence per rasterpoint $\vec{I}=(I_1, I_2, \ldots I_M)$, and the scan path $\vec{S}=(S_1, S_2, \ldots S_M)$. For this purpose, the fluence is an indirect measure how fast or slow a rasterpoint should be irradiated. The scan path indicates the sequence in which the individual rasterpoints should be approached.

For example, from the scan path $\vec{S}$ it is possible to calculate the parameter $S_i - S_{i-1} = |(x,y,z)_i - (x,y,z)_{i-1}|$, which indicates the spatial distance between two rasterpoints in sequence.

The target function $\chi^2$ reads as follows:

$$\chi^2(\vec{N}, \vec{I}, \vec{S}) = \sum_k \left( \frac{D_{pre}^k - D_{act}^k(\vec{N})}{\Delta D_{pre}^k} \right)^2 + \quad (1.1)$$

$$\sum_{i,j} a_i N_i^2 \left( \frac{\delta z^{ij}}{\Delta \delta z^i} \right)^2 + \quad (1.2)$$

$$\sum_{i,j} b_i \left( \frac{\frac{d(\delta z)^{ij}}{dt}(\vec{I}, \vec{S})}{\Delta \left( \frac{d(\delta z)}{dt} \right)^i} \right)^2 + \quad (1.3)$$

$$\sum_{i,j} \frac{c_i}{(I^i - I_{min})^2} + \quad (1.4)$$

$$\sum_{i>2} d_i \left( \frac{S_i - S_{i-1}}{\Delta S^i} \right) \cdot \theta(|S_i - S_{i-1}| - S_{norm}) \quad (1.5)$$

With the following boundary conditions for all i=1 . . . M:

$$N_i \geq N_{min}$$

$$I_i \geq I_{min}$$

$$\Delta \delta z^i = f_{1i} \cdot \delta z_{max}, f_{1i} < 1$$

$$\Delta \left( \frac{d(\delta z)}{dt} \right)^i = f_{2i} \cdot \left( \frac{d(\delta z)}{dt} \right)_{max}, f_{2i} < 1$$

$$\Delta S^i = f_{3i} \cdot S_{norm}, f_{3i} < 1$$

The weightings $a_i$, $b_i$, $c_i$, $d_i$ determine the meaning of the individual summands.

The first summand of the formula describes the deviation of the actual dose $D_{act}^k(\vec{N})$ from the intended dose $D_{pre}^k$.

With the factor $\Delta D_{pre}^k$ the deviation can be weighted by means of voxel more or less strongly.

The second summand of the formula considers motion tracking $\delta z^{ij}$ of the beam in z direction. $\delta z^{ij}$ indicates how great the change is in z direction for a rasterpoint i when transferring from the reference phase to phase j. With the factor $\Delta \delta z^i$,
it is possible to weight these changes per rasterpoint. $\delta z_{max}$ is the maximum tolerable change. For example, in this way, it is possible to consider limitations represented by the system or its interpretation.

The third summand of the formula considers the speed of motion tracking $$\frac{d(\delta z)^{ij}}{dt}$$

of the beam in z direction per rasterpoint and movement phase. This change in speed $$\frac{d(\delta z)^{ij}}{dt}(\vec{I}, \vec{S})$$

depends on the fluence and on the beam path. With the factor $$\Delta \left( \frac{d(\delta z)}{dt} \right)^i,$$

it is possible to weight these changes per rasterpoint.

$$\left( \frac{d(\delta z)}{dt} \right)_{max}$$

is the maximum tolerable speed change. For example, in this way, it is possible to consider limitations represented by the system or its interpretation.

The fourth summand of the formula considers that the fluence per rasterpoint does not become too low during the process of optimization, which would as a whole extend the duration of irradiation.

The fifth summand of the formula considers that the distance of the individual rasterpoints in relation to each other does not become too large when selecting the beam path. With the factor $\Delta S^i$, it is possible to weight the rasterpoints differently. However, by means of the □ function, it can be guaranteed that the distance of the rasterpoints can be selected in any manner as long as they remain below a threshold value $S_{norm}$.

By means of the equation mentioned above, it has been shown how to consider, for example, the beam path, the number of particles to be deposited and the fluence in a target function. With the target function also motion tracking of the particle beam in beam direction is taken into account, so that as a result, it can be guaranteed that motion tracking can be performed by means of the optimized parameters.

Analogous target functions can be used when parameters other than motion tracking, the fluence and the number of particles in z direction should be optimized with respect to beam tracking.

The invention claimed is:

1. Device for determining control parameters for an irradiation system by means of which a number of irradiation doses are successively deposited at different target points in a target volume, comprising:
   an input device which is designed for detecting a target region and for detecting a movement of the target region,
   an evaluation device for detecting control parameters for controlling a beam of the irradiation system in such a way that with the help of the control parameters a beam is able to follow the movement of the target region and to deposit a defined dose distribution in the target region,
   wherein the evaluation device is designed in such a way that, for detecting the control parameters, at least a first selectable control parameter is detected so that the beam is able to follow the movement of the target region merely orthogonally to beam direction, or
   for detecting the control parameters, at least a first selectable control parameter and a further control parameter representing energy modulation of the beam are detected, wherein motion tracking in beam direction is taken into consideration.

2. Device according to claim 1, wherein the evaluation device is designed in such a way that the control parameters are detected in such a way that the beam follows the movement of the target object in at least two different directions.

3. Device according to claim 1, wherein the evaluation device is designed in such a way that in detecting the control parameters a measure is used which takes into consideration motion tracking to be performed in beam direction.

4. Device according to claim 3, wherein the measure considers an amplitude of motion tracking of the beam in beam direction, a speed of motion tracking of the beam in beam direction, and/or a variation of the speed of motion tracking of the beam in beam direction.

5. Device according to claim 1, wherein the evaluation unit is designed in such a way that the measure is incorporated in a target function in which motion tracking of the beam in beam direction is penalized and its evaluation, in particular optimization, contributes to the detection of the control parameters.

6. Device according to claim 1, wherein the evaluation unit is designed in such a way that the at least one first control parameter determines at least a movement phase, during which at least a first section of the target points is not approached.

7. Device according to claim 1, wherein the evaluation unit is designed in such a way that the at least one first control parameter determines a second section of the target points which is approached without performing motion tracking.

8. Device according to claim 1, wherein the evaluation unit is designed in such a way that the at least one first control parameter determines a repeated approach of the target points and/or a succession of the approach of the target points.

9. Device according to claim 1, wherein the evaluation unit is designed in such a way that the at least one first control parameter determines a spatial orientation of a beam inbound direction, a number of beam inbound directions and/or an overlap of target points.

10. Irradiation system with a device for determining control parameters according to any one of claims 1 to 9.

11. Method for determining control parameters for an irradiation system in which a number of irradiation doses can be deposited successively at different target points within a target volume, comprising the following steps:
- detecting a target region with an input device,
- detecting a movement of the target region with the input device,
- detecting control parameters for controlling a beam of the irradiation system in such a way that by means of the control parameters the beam can follow the movement of the target region and a defined dose distribution can be deposited in the target region,
- wherein, when the evaluation unit detects the control parameters, at least a first selectable control parameter is detected in such a way that the beam follows the movement of the target region merely orthogonally to beam direction, or
- wherein, when the evaluation unit detects the control parameters, at least a first selectable control parameter and a further control parameter which represents an energy modulation of the beam, are detected,
- wherein motion tracking in beam direction is taken into consideration.

12. Method for irradiating a moved target region with a set of control parameters for controlling an irradiation system, wherein the control parameters are detected with a method according to claim 11.

13. Method according to claim 12, wherein the target volume comprises at least a portion of a non-living body, in particular a phantom for examining irradiation planning.

* * * * *